United States Patent
Iguchi et al.

(10) Patent No.: US 11,253,532 B2
(45) Date of Patent: Feb. 22, 2022

(54) COMPOSITION FOR PROMOTING INCREASE IN ANDROGEN

(71) Applicant: Kobayashi Pharmaceutical Co., Ltd., Osaka (JP)

(72) Inventors: Kazuaki Iguchi, Shizuoka (JP); Hiroyuki Fukami, Ibaraki (JP)

(73) Assignee: Kobayashi Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 17/071,580

(22) Filed: Oct. 15, 2020

(65) Prior Publication Data
US 2021/0023105 A1 Jan. 28, 2021

Related U.S. Application Data (63) Continuation of application No. 16/474,216, filed as application No. PCT/JP2017/046250 on Dec. 22, 2017, now abandoned.

(30) Foreign Application Priority Data

Dec. 28, 2016 (JP) ................. 2016-256814

(51) Int. Cl.
*A61K 36/258* (2006.01)
*A61K 31/704* (2006.01)

(52) U.S. Cl.
CPC .......... *A61K 31/704* (2013.01); *A61K 36/258* (2013.01)

(58) Field of Classification Search
None
See application file for complete search history.

(56) References Cited

U.S. PATENT DOCUMENTS 8,062,679 B2 * 11/2011 Clement ............... A61K 36/53
424/725
2012/0164269 A1 6/2012 Chen et al.

FOREIGN PATENT DOCUMENTS

| JP | 5204771 B2 | 6/2013 |
| JP | 2015-168614 A | 9/2015 |
| KR | 10-1924389 | 12/2018 |
| WO | 2008/155999 A1 | 12/2008 |

OTHER PUBLICATIONS

Fukami, H. et al. Pharmacokinetic Study of Compound K in Japanese Subjects . . . J of Medicinal Food 22(3)257-263, Mar. 2019. (Year: 2019).*
Lin-Hu Quan et al., "Enzymatic Biotransformation of Ginsenoside Rb1 to Compound K by Recombinant beta-Glucosidase from Microbacterium esteraromaticum," Journal of Agricultural and Food Chemistry, 2012, vol. 60, No. 14, pp. 3776-3781.
International Search Report dated Feb. 6, 2018, issued for PCT/JP2017/046250.
Oh, J. et al., Compound K Derived from Ginseng, Food & Function 7:4506-15, (2016).

* cited by examiner

*Primary Examiner* — Ralph J Gitomer
(74) *Attorney, Agent, or Firm* — Locke Lord LLP; James E. Armstrong, IV; Nicholas J. DiCeglie, Jr.

(57) ABSTRACT

An object of the present invention is to provide a composition for stimulating an increase in an androgen. The composition for stimulating an increase in an androgen contains compound K. The composition for stimulating an increase in an androgen contains a fermentation product and/or enzymatically degraded product of ginseng as an active ingredient.

12 Claims, 1 Drawing Sheet

COMPOSITION FOR PROMOTING INCREASE IN ANDROGEN

CROSS REFERENCE TO RELATED APPLICATIONS

This Application is a Continuation of application Ser. No. 16/474,216 filed on Jun. 27, 2019, which Application is the National Phase entry under 35 U.S.C. § 371 of PCT International Application No. PCT/JP2017/046250, filed Dec. 22, 2017, which application claims priority to Japanese Patent Application No. 2016-256814 filed on Dec. 28, 2016. The entire contents of these applications are incorporated herein by reference in their entirety.

TECHNICAL FIELD

The present invention relates to compositions for stimulating an increase in an androgen.

BACKGROUND ART

Functional decline in gonad has been experimentally and clinically confirmed to occur with aging, due to stress, and other various factors. Testosterone, for example, which is a type of androgens, is known to gradually decrease, in general, from the 20s. Studies report that it is likely that gonadal function declines, bone and muscle diminish, and the amount of body fat increases, along with decreases in testosterone, in middle age and old age (e.g., the age of 45 and above). Studies also report that decreases in androgens are strongly correlated with male menopausal disorder. Developing symptoms associated with decreases in androgens with aging is now sometimes referred to, for example, as late-onset hypogonadism syndrome (LOH syndrome). There is a need to address those symptoms.

Although androgen replacement therapy, for example, is known as a treatment for decreased androgen levels, the therapy is difficult to apply for a long period of time. There are also known side effects, such as liver dysfunction.

Compound K is a known substance, and is also referred to as "20(S)-protopanaxadiol 20-O-β-d-glucopyranoside (M1)," for example. Research reports that compound K has an action to stimulate the secretion of glucagon-like peptide-1 (GLP-1) (PTL 1); however, the influence of compound K on androgen levels remains unknown.

Ginseng contains unique saponins, and is known to be useful in the prevention and improvement of various symptoms, such as anemia, diabetes, and arteriosclerosis. Research also reports that a lactic-acid-bacterial fermentation product or enzymatically degraded product of ginseng has an action to stimulate the secretion of GLP-1 (PTL 1). However, it remains to be seen what effect ginseng and its fermentation product or enzymatically degraded product have on decreased androgen levels.

CITATION LIST

Patent Literature

PTL 1: JP2015-168614A

SUMMARY OF INVENTION

Technical Problem

An object of the present invention is to provide a composition capable of stimulating an increase in androgen levels.

Solution to Problem

The present inventors conducted extensive research to achieve the object, and found that compound K, a fermentation product of ginseng, and an enzymatically degraded product of ginseng can stimulate an increase in androgen levels. The inventors conducted further research on the basis of this finding, and completed the invention described below.

Item 1.
A composition for stimulating an increase in an androgen, the composition comprising compound K.

Item 2.
A composition for stimulating an increase in an androgen, the composition comprising a fermentation product and/or enzymatically degraded product of ginseng as an active ingredient.

Item 3.
The composition according to Item 1 or 2, wherein the androgen is testosterone.

Item 4.
The composition according to any one of Items 1 to 3, wherein the compound K is present in an amount of 0.05 wt % or more in the composition.

Item 5.
The composition according to any one of Items 1 to 4, wherein ginsenoside Rb1 is present in an amount of 10 wt % or less in the composition.

Item 6.
The composition according to any one of Items 2 to 5, wherein the fermentation product is a microbial fermentation product of ginseng.

Item 7.
The composition according to any one of Items 2 to 5, wherein the enzymatically degraded product is a glycosidase hydrolysis product of ginseng.

Item 8.
The composition according to any one of Items 1 to 7, wherein the compound K is present in an amount of 0.12 to 160 mg/60 kg body weight for a daily intake.

Item 9.
The composition according to any one of Items 2 to 8, wherein the fermentation product and/or enzymatically degraded product of ginseng is present in an amount of 19.2 to 24000 mg/60 kg body weight for a daily intake.

Item 10.
The composition according to any one of Items 1 to 9, which is a food composition, a pharmaceutical composition, or a feed composition.

Item 11.
The composition according to any one of Items 1 to 10, for use for a purpose of improving a symptom due to decreased androgen levels.

Advantageous Effects of Invention

The present invention can stimulate the secretion of androgens. The present invention can increase blood androgen levels. Thus, the present invention can stimulate an increase in androgen levels.

DESCRIPTION OF EMBODIMENTS

1. Composition for Stimulating Increase in Androgen that Contains Compound K

The present invention relates to a composition for stimulating an increase in an androgen that contains compound K.

Compound K is a known substance, which is represented by chemical formula $C_{36}H_{62}O_8$; the structure thereof is also known. Compound K is sometimes referred to as "20(S)-protopanaxadiol 20-O-β-d-glucopyranoside (M1)."

Compound K may be derived from a natural source, or may be chemically synthesized; the origin is not limited.

For example, compound K may be a commercially available product. Without any limitation on the present invention, examples of commercially available products of compound K include ginsenoside CK (Extrasynthase), compound K (Matrix Scientific), and ginsenoside compound K (P) (ChromaDex, Inc.).

If compound K is obtained from a natural source, compound K can be suitably obtained from a natural source in accordance with, for example, a known extraction procedure. Examples of natural sources containing compound K include plants; without any limitation on the present invention, examples of such plants include ginseng. From the standpoint of higher efficiency in obtaining compound K, plants are, for example, preferably fermentation products of plants and enzymatically degraded products of plants; and more preferably fermentation products of ginseng and enzymatically degraded products of ginseng.

The part of these plants for use is not particularly limited, as long as the part contains compound K. Any of the root, stalk, leaf, flower, fruit, flower bud, branch, bark, seed, etc., is usable. When the plant is ginseng, the part for use is, for example, preferably the root, more preferably the lateral root and taproot, and still more preferably the lateral root, as described later.

These parts may be used singly, or in a combination of two or more.

The content of compound K in the composition for stimulating an increase in an androgen containing compound K according to the present invention is not limited; and is, for example, preferably 0.05 wt % or more, more preferably 0.05 to 20 wt %, still more preferably 0.1 to 10 wt %, and particularly preferably 0.2 to 5 wt % of the composition.

The content of compound K in the composition according to the present invention is, as stated above, not limited; and can be suitably determined depending on, for example, the physical constitution, age, androgen levels, symptoms, application, and intended use of the subject (target animal). Without any limitation on the present invention, the content of compound K in the composition for a daily intake for an adult with a body weight of 60 kg (reference) is, for example, preferably 0.12 to 160 mg, more preferably 0.12 to 120 mg, still more preferably 0.2 to 75 mg, and particularly preferably 0.4 to 20 mg. The composition according to the present invention may be ingested once daily, or multiple times a day.

The content of ginsenoside Rb1 in the composition according to the present invention is not limited, as long as the effects of the present invention are provided. The content of ginsenoside Rb1 in the composition is, for example, preferably 10 wt % or less, more preferably 2 wt % or less, still more preferably 0.4 wt % or less, and particularly preferably 0.1 wt % or less. Ginsenoside Rb1 is a known substance.

The form of the composition according to the present invention is also not limited, and can be suitably determined depending on the intended use. Examples of the form of the composition according to the present invention include liquid forms, such as solutions, emulsions, suspensions, syrup, extracts, spirits, elixirs, lotions, liniments, injectable drugs, intravenous drips, and suppositories; semi-solid or solid forms, such as powders, granules, subtle granules, tablets, pills, capsules (including hard capsules and soft capsules), patches, troches, chewables, gels, creams, pastes, mousses, ointments, and freeze-dried products in liquid form; and other forms, such as aerosols. For example, a composition according to the present invention in a solid form may be mixed with a liquid, such as water, for use. The composition according to the present invention may also be in a sustained-release dosage form.

The application of the composition according to the present invention is also not limited, and can be suitably determined depending on the intended use. The application of the composition according to the present invention includes food compositions (food with health claims (including food for specified health use, food with nutrient function claims, foods with function claims, and supplements) and food for sick people, including beverages), pharmaceutical compositions; feed compositions; and additives to food compositions, pharmaceutical compositions, feed, etc.

Of these, more specific examples of, for example, food compositions include confectionery (e.g., tablets, candies, chocolate, gum, caramel candies, gummy candies, jelly, yokan (adzuki-bean jelly), manju (Japanese traditional sweets), snacks, cookies, and rice crackers), noodles (e.g., ramen noodle, soba noodle (buckwheat noodle), udon noodle (wheat noodle), and ramen noodle), dairy products (e.g., ice cream, yogurt, and milk), seasonings (e.g., miso (fermented soybean paste) and soy sauce), soup, and beverages (e.g., coffee, tea, carbonated beverages, sports drink, black tea, and juice).

The composition according to the present invention can be produced in accordance with a known typical procedure for the various forms, applications, etc., described above; and can also be produced by optionally adding any components, such as pharmaceutically acceptable components and edible components. Examples of optional components include excipients, disintegrants, diluents, lubricants, flavoring agents, colorants, sweeteners, taste masking agent, suspension agents, moistening agents, emulsifiers, solubilizers, dispersants, buffers, binders, penetration enhancers, stabilizers, extenders, antiseptics, thickening agents, pH adjusters, surfactants, coating agents, absorption promoters, adsorbents, fillers, antioxidants, solubilization agents, seasonings, acidic ingredients, anti-inflammatory agents, algefacients, film-forming agents, gelling agents, amino acids, vitamins, minerals, enzymes, sugars, and various nutritional components. These may be used singly, or in a combination of two or more.

The composition according to the present invention may be orally administered, or parenterally (including transdermally) administered. Examples of parenteral (including transdermal) administration include application of the composition onto the skin or mucosa (external application), and injections. Of these, preferable administration is oral administration.

The subject (target animal) is not limited; and is, for example, a human, and a mammal other than a human. The mammal other than a human includes animals whose androgens play a role in maintaining and improving biological functions. Examples include animals such as mice, rats, guinea pigs, rabbits, dogs, cats, monkeys, swine, cows, and horses; of these, preferable are animals such as mice, rats, guinea pigs, rabbits, dogs, and monkeys.

The composition according to the present invention, with compound K as an active ingredient, can increase androgen levels. Thus, the composition according to the present invention can suppress a decrease in androgens. Accordingly, the present invention can improve various symptoms due to decreased androgens.

Without any limitation on the present invention, examples of the symptoms due to decreased androgens include a range of symptoms associated with late-onset hypogonadism syndromes, such as physical fatigue, mental fatigue, melancholy, anxiety, reduction in appetite, impaired concentration, sleeplessness, a decrease in strength or power (e.g., vibrancy and vigor), an increased feeling of tension, male functional disorder (e.g., decreased sexual desire and erectile dysfunction), cognitive decline, a decrease in motivation or memory ability due to male functional disorder and/or cognitive decline, mental illness (e.g., depression), a rush of blood to the head, hot flash, perspiration, cold limbs, palpitation, rapid pulse, headache, dizziness, tinnitus, limb numbness, increased body fat, obesity, decreased muscle mass, decreased fat metabolism, metabolic syndrome, decreased bone mass, osteoporosis, bone fracture, and poor athletic performance.

Thus, the composition according to the present invention can preferably be applied to a subject who is worried about these symptoms.

From the standpoint of suppressing a decrease in androgens, the composition according to the present invention, without any limitation on the invention, is preferably used in a male whose androgen levels are decreased more than usual, and more preferably a middle-aged or older male or a male who feels very stressed. Thus, the composition according to the present invention is preferably used for the purpose of increasing androgen levels that have been decreased with aging or due to stress. Androgens are a group of steroid hormones, and the major androgen in the living body is testosterone.

The composition according to the present invention includes compositions intended for use in these applications.

Thus, the present invention is also considered to provide a method for producing a compound K-containing composition for stimulating an increase in an androgen. The present invention is also considered to provide a method for stimulating an increase in an androgen characterized by the use of compound K.

Compound K, the composition for stimulating an increase in an androgen, the production method, the androgen-increase-stimulating effect provided by the composition, etc., in these methods are as described above.

2. Composition for Stimulating Increase in Androgen that Contains Fermentation Product and/or Enzymatically Degraded Product of Ginseng as Active Ingredient The present invention relates to a composition for stimulating an increase in an androgen that contains a fermentation product and/or enzymatically degraded product of ginseng as an active ingredient.

In the present invention, ginseng is not particularly limited; and is, for example, preferably ginseng that belongs to the Araliaceae family. Examples of ginseng that belongs to the Araliaceae family include *Otane ginseng* (*Korai ginseng, Korean ginseng: Panax ginseng* C. A. Meyer), *Sanshichi ginseng* (*Panax notoginseng* Burk.), American ginseng (*Panax quinquefolium* L.), *Chikusetsu ginseng* (*Panax japonicus* C. A. Meyer), Himalayan ginseng (*Panax pseudoginseng* Wall. subsp. *himalaicus* Hara), and Vietnamese ginseng (*Panax vietnamensis* Ha et Grushv.). Of these, ginseng is, for example, more preferably *Otane ginseng*.

The part of ginseng for use is not particularly limited. For example, any of the root, stalk, leaf, flower, fruit, flower bud, all parts of the plant, seed, etc., is usable. The part of ginseng for use is, for example, preferably the root, more preferably the lateral root and taproot, and still more preferably the lateral root.

These parts may be used singly, or in a combination of two or more.

In the present invention, the fermentation product of ginseng refers to a product obtained by fermenting ginseng.

Ginseng for use in the preparation of a fermentation product of ginseng may be raw ginseng; or, for example, a dry product, a ground product, a cut product, an extract, a paste, or a suspension of ginseng. Drying, grinding, cutting, extracting, paste-forming, suspending, etc., can be performed in accordance with a known method. These products may also be commercially available products, or those prepared by further suitably treating (e.g., drying) a commercially available product.

These may be used singly, or in a combination of two or more.

Without any limitation on the present invention, the following describes an extract of ginseng as an example. In the present invention, the method for producing an extract (extraction method), extraction conditions, etc., are not particularly limited; a known method can be used.

For example, the part of ginseng for use (raw) is optionally cut, ground, or dried; and subjected to solvent extraction to prepare an extract. Solvent extraction can be performed in accordance with a known method. For example, a known extraction method, such as water (including warm water and hot water) extraction, alcohol extraction, or supercritical extraction, may be used.

For solvent extraction, any solvent is usable. The solvent is, for example, preferably a polar solvent; more preferably an aqueous solution, such as water and physiological saline, an alcohol having 1 to 4 carbon atoms, and any mixture thereof; and still more preferably water, an alcohol having 1 to 4 carbon atoms, and a mixture thereof. Examples of alcohols having 1 to 4 carbon atoms include methanol, ethanol, propanol, and n-butanol. These solvents may be used singly, or in a combination of two or more.

Although the proportion of the ginseng and extraction solvent does not limit the present invention, the extraction solvent is, for example, preferably 300 to 5000 parts by weight, and more preferably 400 to 3000 parts by weight, per 100 parts by weight of ginseng (on a dry weight basis).

When heating is performed in extraction, the heating temperature is, for example, preferably about 15 to 150° C., and more preferably about 20 to 121° C.; however, there is no limitation as long as the effects of the present invention are provided. The heating time is also not limited; and is, for example, preferably about 0.1 to 72 hours, and more preferably about 0.3 to 24 hours.

The obtained extract may be used as is; filtered for use; or further dried for use in a solid form, such as powder or granules. Additionally, the obtained extract may be optionally subjected to purification, concentration, separation of highly active fractions, etc. Without any limitation on the present invention, purification includes treatments such as filtration, and adsorption using ion-exchange resin or activated carbon columns. Available concentration treatments include ordinary methods, such as evaporator. Available separation treatments for highly active fractions include known separation treatments, such as gel filtration, adsorption, silica gel column chromatography, and HPLC (high-performance liquid chromatography).

The thus-obtained extract (or a dried product, a purified product, a concentrated product, or highly active fractions) may be, for example, formed into a powder in accordance with a known method, such as a method for forming powder by subjecting an extract to freeze-drying treatment, for use in the present invention. The extract may also be optionally dissolved in a solvent, such as an alcohol having 1 to 4 carbon atoms.

Additionally, the suspension mentioned above may also be prepared, for example, using the extraction solvents described above as a solvent. The ratio of ginseng to the solvent in the mixture may be suitably determined with reference to the conditions for solvent extraction described above. When heating is performed in the preparation of a suspension, heating can be suitably performed taking into consideration the heating temperature and heating time for the extraction described above.

In the present invention, a fermentation product of ginseng can be obtained by fermenting ginseng. Fermentation can be performed by any method without limitation, as long as ginseng is fermented. Fermentation is preferably performed using microorganisms. From this viewpoint, the fermentation product of ginseng in the present invention is preferably a fermentation product of ginseng by microorganisms (microbial fermentation product of ginseng). Fermentation methods using microorganisms are established. For example, a fermentation product can be prepared with reference to PTL 1 or Japanese Patent No. 520771. Commercially available fermentation products as such are also usable.

Thus, the method for preparing a fermentation product of ginseng is, for example, preferably a method in which ginseng is fermented in the presence of microorganisms to obtain a fermentation product of ginseng; and more preferably a method in which a medium containing ginseng is subjected to sterilization treatment, and the resulting medium is mixed with microorganisms to ferment ginseng to prepare a fermentation product of ginseng. Sterilization can be suitably performed in accordance with a known method, such as heat sterilization, autoclaved sterilization, filter sterilization, etc., unless the effects of the present invention are impaired.

Without any limitation on the present invention, the following describes an example of the procedure for obtaining a microbial fermentation product of ginseng by sterilizing a ginseng-containing medium, and mixing the obtained medium with microorganisms to ferment ginseng.

The medium in the present invention is not limited, as long as microorganisms can be cultured; examples of the medium include those optionally containing various components typically used for the cultivation of microorganisms, such as nitrogen sources, mineral sources, pH buffers, carbon sources, inorganic substances, and water. Such a medium may be a liquid medium, a solid medium, or the like. From the standpoint of preparing a fermentation product of ginseng more efficiently, the medium is preferably a liquid medium.

Without any limitation in this regard, the following describes some components. Examples of nitrogen sources include organic nitrogen sources, including peptones, polypeptones, urea, amino acids, proteins, and peptides such as soybean peptides; and inorganic nitrogen sources, including ammonia and ammonium salts. For example, the nitrogen sources are preferably peptones, polypeptones, peptides, and the like. These nitrogen sources may be used singly, or in a combination of two or more. The concentration of a nitrogen source in a medium may be a typical concentration at which microorganisms can grow, and is not particularly limited. Typically, the concentration of a nitrogen source at the start of culture is preferably about 0.05 to 10 wt %, and more preferably about 0.1 to 5 wt %.

Examples of mineral sources include yeast extracts, meat extracts, potassium, phosphorus, magnesium, and sulfur (e.g., potassium monohydrogen phosphate, and magnesium sulfate).

These mineral sources may be used singly, or in a combination of two or more.

Examples of pH buffers include calcium carbonate.

Examples of inorganic substances include ammonium sulfate, potassium phosphate, magnesium chloride, sodium chloride, iron, manganese, molybdenum, and various vitamins. These inorganic substances may be used singly, or in a combination of two or more.

The pH of the medium is not limited, as long as microorganisms can be cultured. For example, the pH at room temperature (25° C.) is preferably about 3 to 7, and more preferably about 5 to 6.5. The pH may optionally be adjusted with an acid or an alkali.

Without any limitation on the present invention, examples of such a medium include those containing soy peptides, yeast extracts, and calcium carbonate, and the mediums used in the Examples described below.

Sterilization treatment of a ginseng-containing medium can be performed by mixing a medium and ginseng, and sterilizing the resulting medium. Examples of sterilization treatment include the methods described above. From the standpoint of preparing a target fermentation product efficiently, sterilization treatment is preferably autoclaved sterilization.

The amount of ginseng mixed with a medium is also not particularly limited, and may be suitably determined depending on the type of ginseng, the part of ginseng for use, culture conditions, etc. For example, the weight ratio (ginseng/the total amount of a medium) is preferably about 1/100 to 50/100, more preferably about 5/100 to 20/100, and still more preferably about 10/100 to 15/100. The weight ratio as used here refers to a weight ratio calculated based on a dry ginseng prepared by drying ginseng at an internal temperature of about 100 to 180° C. for 1 to 6 hours. The amount of ginseng may be suitably determined with reference to these values. The medium may optionally contain additives other than ginseng and ingredients described above, unless the effects of the present invention are impaired.

Microorganisms for use in the present invention are also not limited, as long as the effects of the present invention are provided. Such microorganisms are, for example, preferably Gram-positive bacteria, and more preferably lactic acid bacteria. From this viewpoint, the microbial fermentation product of ginseng according to the present invention is, for example, preferably a fermentation product of ginseng by Gram-positive bacteria (a Gram-positive bacterial fermentation product of ginseng), and more preferably a fermentation product of ginseng by lactic acid bacteria (a lacticacid-bacterial fermentation product of ginseng). These microorganisms may be used singly, or in a combination of two or more.

The microorganisms are, for example, more preferably those that can produce at least one enzyme selected from the group consisting of β-glucosidase, α-arabinosidase, and α-rhamnosidase, and that can be added to foods.

Although the present invention is not limited in this regard, examples of microorganisms that can produce the enzymes described above include lactic acid bacteria of genus *Lactobacillus*, such as *Lactobacillus acidophilus*, *Lactobacillus gasseri* (*L. gasseri*), *Lactobacillus mali* (*L. mali*), *Lactobacillus plantarum* (*L. plantarum*), *Lactobacillus buchneri* (*L. buchneri*), *Lactobacillus casei* (*L. casei*), *Lactobacillus johnsonii* (*L. johnsonii*), *Lactobacillus gallinarum* (*L. gallinarum*), *Lactobacillus amylovorus* (*L. amylovorus*), *Lactobacillus brevis* (*L. brevis*), *Lactobacillus rhamnosus* (*L. rhamnosus*), *Lactobacillus kefir* (*L. kefir*), *Lactobacillus paracasei* (*L. paracasei*), and *Lactobacillus crispatus* (*L. crispatus*); lactic acid bacteria of genus *Streptococcus*, such as *Streptococcus thermophilus*; lactic acid bacteria of genus *Lactococcus*, such as *Lactococcus lactis*; lactic acid bacteria of genus *Bifidobacterium*, such as *Bifidobacterium bifidum*, *Bifidobacterium longum* (*B. longum*), *Bifidobacterium adolescentis* (*B. adolescentis*), *Bifidobacterium infantis* (*B. infantis*), *Bifidobacterium breve* (*B. breve*), and *Bifidobacterium catenulatum* (*B. catenulatum*); bacteria of genus *Bacillus*, such as *Bacillus subtilis*; yeasts of genus *Saccharomyces*, such as *Saccharomyces cerevisiae*; yeasts of genus *Torulaspora*, such as *Torulaspora delbrueckii*; and yeasts of genus *Candida*, such as *Candida kefir*.

Of these, preferable are lactic acid bacteria; and more preferable are lactic acid bacteria of genus *Lactobacillus*, lactic acid bacteria of genus *Streptococcus*, lactic acid bacteria of genus *Lactococcus*, lactic acid bacteria of genus *Bifidobacterium*, and yeasts of genus *Saccharomyces*.

These microorganisms may be used singly, or in a combination of two or more.

Without any limitation on the present invention, examples of lactic acid bacteria of genus *Lactobacillus* include *Lactobacillus casei* strain Hasegawa (accession number: FERM BP-10123, accession date: Aug. 11, 2003), *Lactobacillus gasseri* DSM20243 strain, *Lactobacillus plantarum* ATCC14947 strain, *Lactobacillus plantarum* ATCC10241 strain, *Lactobacillus buchneri* ATCC4005 strain, *Lactobacillus casei* ATCC393 strain, *Lactobacillus mali* ATCC27304 strain, *Lactobacillus gallinarum* JCM2011 strain, *Lactobacillus amylovorus* JCM1126 strain, *Lactobacillus brevis* ATCC14869 strain, *Lactobacillus rhamnosus* ATCC7469 strain, *Lactobacillus rhamnosus* ATCC53103 strain, *Lactobacillus kefir* NRIC1693 strain, and *Lactobacillus paracasei* NCDO-151 strain.

Examples of lactic acid bacteria of genus *Lactococcus* include *Lactococcus lactis* ATCC15577 strain.

Examples of lactic acid bacteria of genus *Bifidobacterium* include *Bifidobacterium bifidum* JCM7002 strain, and *Bifidobacterium adolescentis* ATCC15703 strain.

Examples of yeasts of genus *Saccharomyces* include *Saccharomyces cerevisiae* IFO-0309 strain, and *Saccharomyces cerevisiae* IFO-2018 strain.

These microorganisms may be used singly, or in a combination of two or more.

Of these microorganisms, *Lactobacillus casei* strain Hasegawa, for example, is particularly preferable. This bacterial strain is a microorganism isolated from a common food, such as Japanese pickles, and is safe to ingest. For example, it is known that this bacterial strain efficiently produces compound K from ginseng in a fermentation product of ginseng.

In the present invention, the conditions under which a medium and microorganisms are mixed are not limited, as long as ginseng can be fermented. For example, when the ginseng-containing medium described above is mixed with a culture solution prepared by culturing microorganisms in a liquid medium beforehand, preferably about 0.01 to 10 parts by weight of the culture solution is mixed with 100 parts by weight of the ginseng-containing medium; and more preferably about 0.1 to 5 parts by weight of the culture solution is mixed with 100 parts by weight of the ginseng-containing medium.

The liquid medium for culturing microorganisms beforehand is not limited, as long as microorganisms can grow; and can be suitably determined depending on, for example, the type of microorganisms for use. An example is the mediums described in the Examples detailed later.

The pH of the medium after mixing in the present invention is not limited, as long as microorganisms can grow, and as long as ginseng can be fermented. The pH can be suitably determined depending on, for example, the type of microorganisms for use. In an embodiment, the pH is preferably adjusted to about 4 to 7.

The temperature for fermentation of ginseng after mixing in the present invention is not limited, as long as fermentation is possible; and can be suitably determined depending on, for example, the formula of the medium, the type of microorganisms, and the amount of microorganisms. From the standpoint of performing fermentation more efficiently, the temperature for fermentation is, for example, preferably about 25 to 37° C., and more preferably about 28 to 33° C. The fermentation time is also not limited, as long as fermentation is possible; and can be suitably determined depending on, for example, the formula of the medium, the type of microorganisms, the amount of microorganisms, and the fermentation temperature. The fermentation time is, for example, preferably about 2 to 21 days, and more preferably about 7 to 14 days. Fermentation may be performed under aerobic conditions, or under anaerobic conditions. After fermentation, it is preferable to perform heating sterilization in accordance with an ordinary method.

After fermentation, the resulting fermented liquid may be used without any treatment as a component of the composition according to the present invention; or may be used after any treatment, such as concentration, drying, purification, extraction, and dilution, as a component of the composition according to the present invention. Examples of concentration methods include a method in which a fermented liquid is concentrated; a method in which the obtained fermented liquid is allowed to stand, and the supernatant is collected, followed by concentration of the collected supernatant; and a method in which a supernatant is extracted, and concentrated. Examples of drying methods include a method in which the fermented liquid, the supernatant, the extract, or the concentrate are dried. Examples of purification methods include filtration and centrifugation. These can be suitably performed in accordance with a known technique.

In the present invention, the thus-obtained product may be referred to as a "microbial fermentation product of ginseng."

In the present invention, the enzymatically degraded product of ginseng indicates a product obtained by enzymatically treating ginseng.

To obtain an enzymatically degraded product of ginseng, enzymatic degradation can be performed in accordance with a known method. A method for enzymatic degradation is fully established (e.g., the method according to J. Agric. Food. Chem. 2012, 60 (14): 3776-81). Without any limitation in this regard, the following describes an example of a method for producing an enzymatically degraded product of ginseng.

Enzymatic degradation of ginseng can be performed by bringing ginseng into contact with an enzyme.

Ginseng is as described above.

The enzyme for use in enzymatic degradation of ginseng is, for example, preferably a glycosidase, more preferably β-glucosidase, α-arabinosidase, α-rhamnosidase, α-galactosidase, β-galactosidase, xylanase, lactase, α-amylase, β-amylase, cellulase, and hemicellulase. The enzyme for use in enzymatic degradation is still more preferably β-glucosidase, α-arabinosidase, and α-rhamnosidase, and particularly preferably β-glucosidase. These enzymes may be used singly, or in a combination of two or more. If a glycosidase is used for the enzyme, the enzymatically degraded product of ginseng in the present invention can also be referred to as a glycosidase hydrolysis product of ginseng.

The temperature at which ginseng is in contact with an enzyme for enzymatic degradation (reaction temperature) is not limited, as long as the effects of the present invention are provided. The reaction temperature can be suitably determined depending on, for example, the type of enzyme for use, the type of ginseng for use, and the amount of the enzyme and ginseng. The reaction temperature is, for example, preferably about 10 to 90° C., and more preferably about 30 to 50° C.

The time during which ginseng is in contact with an enzyme (reaction time) is also not limited, as long as the effects of the present invention are provided. The reaction time can be suitably determined depending on, for example, the type of enzyme for use, the type of ginseng for use, the amount of the enzyme and ginseng, and the treatment temperature. The reaction time is, for example, preferably about 1 hour to 2 weeks, and more preferably about 4 hours to 1 week.

After this reaction, the obtained reaction product may be used without any treatment as a component of the composition according to the present invention; or may be used after a treatment, such as concentration, drying, purification, extraction, and dilution, as a component of the composition according to the present invention. Details of the treatments are as described above for the treatments of the microbial fermentation product of ginseng.

From the standpoint of more efficiently bringing ginseng into contact with an enzyme in order to obtain an enzyme reaction product more efficiently, the resulting reaction product is preferably in the form of a reaction solution. Examples of concentration methods for such a reaction solution include a method in which an obtained reaction solution is concentrated; a method in which an obtained reaction solution is allowed to stand, and the supernatant is collected, followed by concentrating the collected supernatant; and a method in which a supernatant is extracted, and concentrated. Examples of drying methods include a method in which the reaction solution, the supernatant, the extract, or the concentrate is dried. Examples of purification methods include filtration and centrifugation. These can be suitably performed in accordance with a known technique.

In the present invention, the thus-obtained product may be referred to as an "enzymatically degraded product of ginseng." Compound K can also be efficiently produced from ginseng in this enzymatically degraded product of ginseng.

Compound K is produced, for example, due to cleavage of sugar from ginsenoside Rb1 contained in *Korai ginseng*; and enzymatic degradation, as with fermentation, promotes the production of compound K from ginsenoside Rb1 in the present invention. Thus, the fermentation product of ginseng and the enzymatically degraded product of ginseng according to the present invention preferably have a higher content of compound K than untreated ginseng, and more preferably have a higher content of compound K relative to ginsenoside Rb1 than untreated ginseng. Thus, the fermentation product of ginseng or the enzymatically degraded product of ginseng can stimulate an increase in androgen levels.

The content of the fermentation product and/or enzymatically degraded product of ginseng in the composition according to the present invention is not limited, and can be suitably determined depending on, for example, the physical constitution, age, androgen levels, symptoms, applications, and intended use of the subject (target animal). Without any limitation on the present invention, the content of the fermentation product and/or enzymatically degraded product of ginseng in the composition (total amount thereof) for a daily intake for an adult with a body weight of 60 kg is, for example, preferably 19.2 to 24000 mg, more preferably 30 to 8000 mg, and sill more preferably 40 to 2000 mg. The composition according to the present invention may be administered once daily, or multiple times daily.

Without any limitation on the present invention, compound K is present, for example, in an amount of preferably 0.05 wt % or more, more preferably 0.05 to 20 wt %, still more preferably 0.1 to 10 wt %, and particularly preferably 0.2 to 5 wt % in the composition for stimulating an increase in an androgen containing the fermentation product and/or enzymatically degraded product of ginseng as an active ingredient according to the present invention.

Although there is no limitation as long as the effects of the present invention are obtained, ginsenoside Rb1 is present, for example, in an amount of preferably 10 wt % or less, more preferably 2 wt % or less, still more preferably 0.4 wt % or less, and particularly preferably 0.1 wt % or less in the composition according to the present invention. Ginsenoside Rb1 is a known substance.

The form of the composition according to the present invention is also not limited, and can be suitably determined according to the intended use. The form of the composition according to the present invention is as explained in the above section "1. Composition for Stimulating Increase in Androgen That Contains Compound K," and examples of the form of the composition according to the present invention include liquid forms, such as solutions, emulsions, suspensions, syrup, extracts, spirits, elixirs, lotions, liniments, injectable drugs, intravenous drips, and suppositories; semi-solid or solid forms, such as powders, granules, subtle granules, tablets, pills, capsules (including hard capsules and soft capsules), patches, troches, chewables, gels, creams, pastes, mousses, ointments, and freeze-dried products in liquid form; and other forms, such as aerosols. For example, a composition according to the present invention in a solid form may be mixed with a liquid, such as water, for use. The composition according to the present invention may also be in a sustained-release dosage form.

The application of the composition according to the present invention is also not limited, and can be suitably determined depending on the intended use. The application of the composition according to the present invention is as explained in the above section "1. Composition for Stimulating Increase in Androgen That Contains Compound K." Specifically, the application of the composition according to the present invention includes food compositions (food with health claims (including food for specified health use, food with nutrient function claims, foods with function claims, and supplements) and food for sick people, including beverages), pharmaceutical compositions, feed compositions; and additives to food compositions, pharmaceutical compositions, feed, etc.

The composition according to the present invention can be produced in accordance with a known typical procedure for the various forms, applications, etc., described above; and can also be produced by optionally adding any components, such as pharmaceutically acceptable components and edible components. Examples of the optional components are as explained in the above section "1. Composition for Stimulating Increase in Androgen That Contains Compound K."

The composition according to the present invention may be orally administered, or parenterally (including transdermally) administered. Examples of parenteral (including transdermal) administration include application of the composition onto the skin or mucosa (external application), and injections. Of these, preferable administration is oral administration.

The subject (target animal) is also not limited, and the subject (target animal) is as described above.

The composition according to the present invention, with a fermentation product and/or enzymatically degraded product of ginseng as an active ingredient, can increase androgen levels. Thus, the composition according to the present invention can suppress a decrease in androgens. Accordingly, the present invention can improve various symptoms due to decreased androgens. The symptoms due to decreased androgens are as described above. Thus, the composition according to the present invention may preferably be applied to a subject who is worried about these symptoms.

From the standpoint of suppressing a decrease in androgens, the composition according to the present invention, without any limitation on the invention, is preferably used in a male whose androgen levels are decreased more than usual, and more preferably a middle-aged or older male or a male who feels very stressed. Thus, the composition according to the present invention is preferably used for the purpose of increasing androgen levels that have been decreased with aging or due to stress. Androgens are, as described above, a group of steroid hormones, and the major androgen in the living body is testosterone.

The composition according to the present invention includes compositions intended for use in these applications.

Thus, the present invention is also considered to provide a method for producing a composition for stimulating an increase in an androgen containing a fermentation product and/or enzymatically degraded product of ginseng as an active ingredient. The present invention is also considered to provide a method for stimulating an increase in an androgen characterized by the use of a fermentation product and/or enzymatically degraded product of ginseng.

The fermentation product of ginseng, the enzymatically degraded product of ginseng, the composition for stimulating an increase in an androgen, the production method, the androgen-increase-stimulating effect provided by the composition, etc., in these methods are as described above.

EXAMPLES

The following describes the present invention with reference to Examples. However, the present invention is not limited to the Examples.

Test Example 1

The effect of compound K on androgen secretion was evaluated in accordance with the following procedure.

Sample (Compound K)

2 mL of 50% ethanol was added to 4 mg/vial of compound K (trade name: Ginsenoside CK, 0150S, Extrasynthese S.A.) to dissolve compound K, and the obtained solution was suitably diluted with a DME/F-12 medium (Nacalai Tesque) containing 0.1% bovine serum albumin (BSA) ("0.1% BSA-DME/F-12") to prepare a sample.

Evaluation Procedure

Testes were collected from mice (ddY strain, male, 7 to 8 weeks old), and subjected to primary culture. Specifically, testes were subjected to collagenase treatment (Worthington, Type 2, 0.05%, 37° C., 15 minutes) to disperse cells, and adjusted to $3 \times 10^5$ cells/0.5 mL in a DME/F-12 medium containing 10% fetal bovine serum (FBS). The cells were then seeded into a 24-well plate, and cultured overnight. After culture, the cells were washed with PBS(−) (Dulbecco's PBS (0.2 g/L of potassium chloride, 0.2 g/L of monopotassium phosphate, 8 g/L of sodium chloride, 1.15 g/L of anhydrous disodium phosphate, pH of 7.4, an isotonic solution, ion content: (mEq)$Na^+$ 148, $K^+$ 4, $Cl^-$ 139)). The prepared sample was then added to the cells to give a volume of 1/10, together with a 0.1% BSA-DME/F-12 medium, and the concentration of compound K in the wells was adjusted to 1 μg/mL, 10 μg/mL, and 100 μg/mL.

A mixture solution of 50% ethanol and 0.1% BSA-DME/F-12 was prepared in place of the sample in the same manner as above, except that compound K was not added; this mixture was added to the cells to give a volume of 1/10 as above, thereby preparing a control (the concentration of compound K: 0 μg/mL).

After 2-hour culture, the medium was collected, and the testosterone levels in the mediums were measured by enzyme immunoassay (EIA).

Specifically, a goat anti-rabbit IgG antibody (2 μg/well) was added to a 96-well microplate (Nunc, Denmark), and the plate was coated at room temperature for 1 hour. After washing, a blocking agent (0.14M NaCl, 0.02% thimerosal, 1% BSA, 0.01M phosphate buffer, pH of 7.4) was added thereto to perform blocking at room temperature for 15 minutes. After washing, the collected medium, testosterone (Wako Pure Chemical Industries, Ltd.) (standardized antigen), biotinylated testosterone (labeled antigen), and anti-testosterone serum were sequentially added, and a reaction was allowed to proceed for 2 hours. After washing, HRP-labeled avidin (diluted 10,000-fold, Jackson ImmunoResearch Laboratories, Inc.) was added, and the mixture was stirred to allow a reaction to proceed for 30 minutes. After washing, a 0.002% ortho-phenylene diamine solution (dissolved in a citric phosphate buffer containing 0.0012% hydrogen peroxide) was added to allow a color reaction to proceed for 10 minutes, and the reaction was ended with 2M sulfuric acid. The absorbance at 490 nm was measured with a microplate reader to determine the testosterone secretion level.

Results

Figure 1:
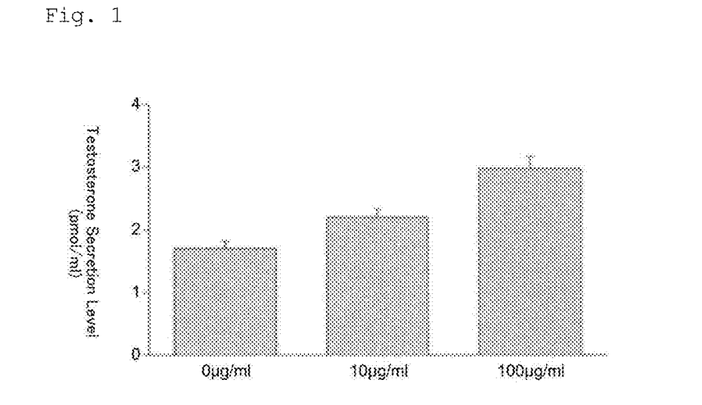
FIG. 1 illustrates changes in testosterone secretion level due to addition of compound K.

FIG. 1 illustrates the results (average±standard error of the mean, the number of specimens: 4 each). As is clear from FIG. 1, the mediums containing compound K exhibited a higher testosterone level than the medium free from compound K (indicated as "0 μg/mL" in FIG. 1). Specifically, the testosterone level in a medium was higher in both cases of the compound K content: 10 μg/mL and 100 μg/mL. Although not shown in FIG. 1, the addition of 1 μg/mL of compound K also exhibited an increased testosterone level in a medium. This indicates that compound K can significantly stimulate the secretion of testosterone from cells.

Test Example 2

The effect of ginseng on androgen secretion was evaluated in accordance with the following procedure.

Sample (Ginseng)

A fermentation product of ginseng was prepared using *Lactobacillus casei* strain Hasegawa (accession number: FERM BP-10123). Specifically, a loopful of *Lactobacillus casei* strain Hasegawa was seeded into 20 mL of a medium (glucose 30 g/L, yeast extract 10 g/L, soybean peptide 5 g/L, $K_2HPO_4$ 2 g/L, $MgSO_4 \cdot 7H_2O$ 0.5 g/L), and subjected to stationary culture at 28° C. for 48 hours. Subsequently, 2 mL of the obtained culture solution was added to 120 mL of a fresh medium (the same formula as above), and subjected to stationary culture at 28° C. for 48 hours. 20 mL of the obtained culture solution was added to 1 L of a solution for fermentation (130 g/L of *Otane ginseng* (lateral root) powder, 10 g/L of yeast extract, 5 g/L of soybean peptides, and 10 g/L of calcium carbonate) that was previously subjected to autoclaved sterilization (at 121° C. for 20 minutes); and fermented at 28° C. for 10 days. The obtained fermented solution was adjusted to a pH of 5.0 with sodium hydroxide; and subjected to spray-drying, thereby preparing an *Otane ginseng* fermentation product.

1000 mg of the obtained *Otane ginseng* fermentation product was mixed with 10 mL of 50% ethanol or 10 mL of water, and subjected to reverse-stirring at room temperature for 1 hour. The solution was then centrifuged (4000 rpm, 15 minutes). The obtained supernatant (extract) was stored at −20° C. until use. Before use, the extract was suitably diluted with a 0.1% BSA-DME/F-12 medium. The sample that was extracted with ethanol and the sample that was extracted with water are respectively referred to as sample E and sample W.

For the Comparative Example, an extract of a non-fermentation product was used. Specifically, 1000 mg of *Otane ginseng* (lateral root) powder was mixed with 10 mL of 50% ethanol or 10 mL or water, and subjected to reverse-stirring at room temperature overnight. The solution was then centrifuged as above, and the supernatant was obtained as an extract of a non-fermentation product. The extract was stored at −20° C. until use as above, and diluted with a 0.1% BSA-DME/F-12 medium before use. The comparative sample that was extracted with ethanol and the comparative sample that was extracted with water are respectively referred to as comparative sample E and comparative sample W.

Evaluation Procedure

In the same manner as in the Test Example above, testes were subjected to collagenase treatment to disperse the cells, and the obtained cells were seeded into a well-plate using a DME/F-12 medium containing 10% FBS ($1.5 \times 10^5$ cells/well), followed by culture overnight. After culture, the cells were washed with PBS(−); sample E, sample W, comparative sample E, or comparative sample W prepared as described above was added to the cells together with a 0.1% BSA-DME/F-12 medium to achieve 1 mg equivalent of the *Otane ginseng* fermentation product or *Otane ginseng* (lateral root) powder/mL (final concentration in wells). After 2-hour culture, each medium was collected, and the testosterone level in the mediums was measured by EIA in the same manner as above.

Results

Figure 2:
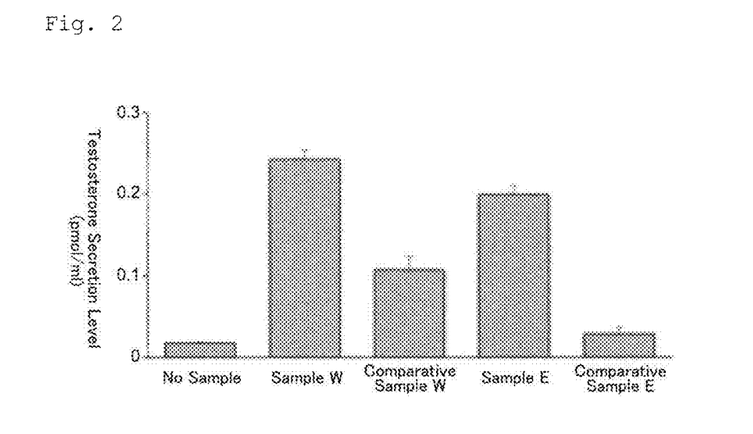
FIG. 2 illustrates changes in testosterone secretion level due to addition of fermentation products of ginseng.

FIG. 2 illustrates the results (average±standard error of the mean, the number of specimens: 4 each). The testosterone level in a medium that was prepared in the same manner using none of samples E and W, or comparative samples E and W, is indicated as "No Sample" in FIG. 2.

As is clear from FIG. 2, the mediums containing sample E or sample W exhibited a significantly increased testosterone level compared with the medium free from the samples. Although the medium containing comparative sample W also exhibited an increased testosterone level in the medium, the effect was considerably inferior to that of the mediums containing sample E or sample W. Comparative sample E exhibited no significant increase. This indicates that the fermentation product of ginseng can significantly stimulate the secretion of testosterone from cells.

Test Example 3

The effect of ginseng on blood androgen levels was evaluated in accordance with the following procedure.

Sample

An *Otane ginseng* fermentation product was prepared in the same manner as in Test Example 2. The obtained fermentation product (powder) was mixed with water, and liquid samples containing the fermentation product with a concentration of 2000 mg/10 mL, 400 mg/10 mL, 80 mg/10 mL, or 16 mg/10 mL (samples 1 to 4, in this order) were prepared. Water, instead of the liquid samples, was used as the control.

Evaluation Procedure

Rats (Wistar strain, male, 13 weeks old) were reared in rat cages (a plastic cage with a stainless-mesh cover, one rat/cage) on ad libitum feeding with commercially available solid feed (trade name: CE-2, CLEA Japan, Inc.) and water for 7 days. The rats were allotted into groups based on body weight before sample administration to avoid variation between tests (4 rats per group). A necessary dose was calculated based on 1.0 mL per 100 g of rat body weight at the time a sample was administered, and the prepared samples 1 to 4 were administered to rats by oral gavage. The forced administration was performed twice, in the morning and afternoon, daily at an interval of at least 6 hours between doses. The control group that was scheduled to be given water was subjected to oral gavage of 0.5 mL of water per 100 g of rat body weight in the same manner. The administration of a sample or water was performed for 21 consecutive days.

Additionally, the rats were subjected to restraint stress for 5 days from day 11 to day 16 after the start of peroral administration of the samples. Specifically, the rats were placed under restraint stress by being reared in a Ballman cage (KN-326-2-A, Natsume Seisakusho Co., Ltd.) for 5 days with feeding of the samples or water. After being under restraint stress for 5 days, the rats were released from the stress, and again placed under feeding conditions applied before restraint stress (peroral administration of the samples or water without restraint stress).

Blood was collected immediately before the rats were placed in a Ballman cage (day 11 after the start of peroral administration of the samples), and after 5 days from the release of the rats from restraint stress (day 21 after the start of peroral administration of the samples). The blood testosterone levels were then measured. Specifically, blood collection was performed as follows: blood was taken from the caudal artery or jugular vein (about 0.7 mL), placed in a sample tube, and centrifuged to collect serum, followed by analyzing the free testosterone level by ELISA.

Specifically, free testosterone levels were analyzed using a Free Testosterone ELISA (DB52181, IBL International) kit. The procedure stated in the manual of the kit was followed: the collected serum, a standardized antigen (testosterone), and a control antigen (testosterone) were added to a well-plate on which an anti-testosterone monoclonal antibody was solid-phased beforehand; and HRP-labeled testosterone was then added thereto, followed by a reaction for 1 hour. After washing, a substrate solution (tetramethylbenzidine) was added to perform color reaction, and the reaction was ended with 1M sulfuric acid. The absorbance at 450 nm was measured with a microplate reader to determine the free testosterone level in serum.

Results

Table 1 illustrates the results. Table 1 indicates the free testosterone level in blood of each group before stress application as 1. As is clear from Table 1, the free testosterone level in blood of the control group significantly decreased to 0.36 by placing the rats under stress. In contrast, the groups that were given samples 1 to 4 all exhibited a higher free testosterone level in blood after stress application than the control group after stress application, indicating a significant suppression of decreases in free testosterone levels in blood due to stress application.

This reveals that a fermentation product of ginseng can suppress decreases in free testosterone level in blood.

TABLE 1

|  | Relative Free Testosterone Level | | | | |
| --- | --- | --- | --- | --- | --- |
|  | Control | Sample 1 | Sample 2 | Sample 3 | Sample 4 |
| Before Stress Application | 1 | 1 | 1 | 1 | 1 |
| After 10 Days from the Start of Stress Application | 0.36 | 0.56 | 0.63 | 0.67 | 0.40 |

When the results are converted to a dose for humans based on a CRC textbook (the training guidelines for CRC certified by the Japanese Society of Clinical Pharmacology and Therapeutics), the daily dosage of the fermentation product of ginseng is 19.2 mg to 24000 mg/body (60 kg)/day. When the results are converted based on the content of compound K in the fermentation product of ginseng, the daily dosage of compound K is 0.123 to 154 mg/body (60 kg)/day.

Test Example 4

Procedure

The effect of ginseng on androgen levels was evaluated in accordance with the following procedure.

Twelve mice (ddY, male, 7 weeks old, Japan SLC, Hamamatsu) were divided into three groups: a normal feed group under no stress (normal feed group with no stress application); a normal feed group under stress (a normal feed group with stress application); and a group fed a fermentation product of ginseng under stress (a group fed fermented ginseng with stress application).

The normal feed group with no stress application and the normal feed group with stress application were allowed to freely eat a standard powder feed (MF, Oriental Yeast Co., ltd.) for 2 weeks. The group fed fermented ginseng with stress application was allowed to freely eat a feed prepared by mixing the standard powder with an *Otane ginseng* fermentation product (powder) prepared, to give a content of 5 wt %, in the same manner as in Test Example 2 for 2 weeks. The mice were reared in cages (one mouse per cage), with free intake of water, at an adjusted temperature (23±1° C.) and humidity (55±5%) in a 12-hour light-dark cycle (light period: 8:00-20:00, dark period: 20:00-8:00). The mice with stress application were restrained in a plastic test tube from 20:00 to 8:00, 3 times in total after the start of test (day 11, day 12, and day 13) for stress application. The mice were then released from stress at 8:00 on day 14. Three hours after release, the mice were dissected to collect testes; and the testes were put together for each group, followed by primary culture.

The primary culture was performed in accordance with the method shown in Test Example 1 (the number of cells per well was $3 \times 10^5$), and the testosterone secretion level in the culture solution obtained after 2 hours of culture was measured by EIA in the same manner as in Test Example 1.

Results

While the normal feed group with stress application exhibited a significantly lower testosterone secretion level than the normal feed group with no stress application, the group fed fermented ginseng with stress application exhibited a curbed decrease in secretion level. This indicates that the ingestion of the fermentation product of ginseng helps to increase testosterone secretion in a stressful environment.

This reveals that administering compound K or a fermentation product of ginseng can suppress the decrease in androgen levels. Additionally, this also reveals that an enzymatically degraded product of ginseng that stimulates the production of compound K can also suppress the decrease in androgen levels.

The invention claimed is:

1. A method for stimulating an increase in an androgen, the method comprising administering to a subject in need of stimulating an increase in an androgen a composition comprising an effective amount of 20(S)-protopanaxadiol 20-O-beta-d-glucopyranoside (compound K) and a pharmaceutically acceptable component or an edible component.

2. The method according to claim 1, wherein the androgen is testosterone.

3. The method according to claim 1, wherein the compound K is present in an amount of 0.05 wt % or more in the composition.

4. The method according to claim 1, wherein ginsenoside Rb1 is present in an amount of 10 wt % or less in the composition.

5. The method according claim 1, wherein the compound K is administered to the subject in an amount of 0.12 to 160 mg/60 kg body weight for a daily intake.

6. The method according claim 1, the composition is a food composition, a pharmaceutical composition, or a feed composition.

7. A method for improving a symptom due to decreased androgen level, the method comprising administering to a subject in need of improving a symptom due to decreased androgen level a composition comprising an effective amount of compound K and a pharmaceutically acceptable component or an edible component.

8. The method according to claim 7, wherein the androgen is testosterone.

9. The method according to claim 7, wherein the compound K is present in an amount of 0.05 wt % or more in the composition.

10. The method according to claim 7, wherein ginsenoside Rb1 is present in an amount of 10 wt % or less in the composition.

11. The method according claim 7, wherein the compound K is administered to the subject in an amount of 0.12 to 160 mg/60 kg body weight for a daily intake.

12. The method according claim 7, the composition is a food composition, a pharmaceutical composition, or a feed composition.

* * * * *